United States Patent [19]
Grinnell

[11] Patent Number: 5,618,714
[45] Date of Patent: Apr. 8, 1997

[54] METHODS FOR PRODUCING PROTEIN C

[75] Inventor: Brian W. Grinnell, Indianapolis, Ind.

[73] Assignee: Eli Lilly and Company, Indianapolis, Ind.

[21] Appl. No.: 168,035

[22] Filed: Dec. 15, 1993

[51] Int. Cl.$^6$ .............................. C12N 5/10; C12N 5/16; C12Q 1/37; C12P 21/00
[52] U.S. Cl. .............................. 435/226; 435/23; 435/29; 435/69.1; 435/375
[58] Field of Search .................................. 435/226, 69.1, 435/23, 29

[56] References Cited

U.S. PATENT DOCUMENTS

| | | | |
|---|---|---|---|
| 4,775,624 | 10/1988 | Bang et al. | 435/226 |
| 4,959,318 | 10/1990 | Foster et al. | 435/172.3 |
| 4,968,626 | 11/1990 | Foster et al. | 435/320.1 |
| 4,981,952 | 1/1991 | Yan | 530/384 |
| 4,992,373 | 2/1991 | Bang et al. | 435/69.6 |
| 5,073,609 | 12/1991 | Foster et al. | 536/23.2 |

FOREIGN PATENT DOCUMENTS

| | | |
|---|---|---|
| 0245949 | 11/1987 | European Pat. Off. |
| 0323149 | 12/1988 | European Pat. Off. |
| 0354504 | 8/1989 | European Pat. Off. |
| 0363127 | 4/1990 | European Pat. Off. |
| 0445939 | 9/1991 | European Pat. Off. |
| 88/03926 | 6/1988 | WIPO |
| 91/02065 | 2/1991 | WIPO |
| 92/13079 | 8/1992 | WIPO |

OTHER PUBLICATIONS

Berg, et. al., 1993, Bio/Techniques 14:6, 972–978.
Grinnell et. al., 1987 Bio/Technology 5:1187–1192.
Berg, et. al., 1989, Mol. Cell. Biol. 9(11):5248–5253.
Berg, et. al., 1991, Exp. Cell Res. 192:32–40.
Ehrlich, et. al., 1989, J. Biol. Chem. 264(24):14298–14304.
Yan, et. al., 1990, Bio/Technology 8:655–661.
Grinnell, et. al., 1989, Genetics and Molecular Biology of Industrial Microorganisms (Hershberger et. al., eds.) pp. 226–237, American Society for Microbiology, Washington, D.C.
Walls, et. al., 1989, Gene 81:139–149.
Grinnell, et. al., 1991, J. Biol. Chem. 226:9778–9785.
Keeton, Biological Science, 3$^{rd}$ Edition, W.W. Norton & Co., New York, New York, 1980, pp. 70–73.

Primary Examiner—Dian C. Jacobson
Assistant Examiner—Eric Grimes
Attorney, Agent, or Firm—Douglas K. Norman; David E. Boone

[57] ABSTRACT

The present invention relates to a method for producing high levels of functional recombinant proteins in adenovirus-transformed mammalian cells by incubating cells capable of producing recombinant proteins at a temperature range between about 38 degrees centigrade and about 39 degrees centigrade. The method allows for higher levels of expression of total protein in some cell lines and higher levels of functional protein in other cell lines.

7 Claims, No Drawings

5,618,714

METHODS FOR PRODUCING PROTEIN C

FIELD OF THE INVENTION

This invention relates to molecular biology, particularly to methods for the production of high levels of functional recombinant protein C in mammalian cell lines.

SUMMARY OF THE INVENTION

Many proteins undergo extensive post-translational modification during maturation. Human Protein C (HPC) is gamma-carboxylated, beta-hydroxylated and glycosylated either during or soon after translation of the primary RNA transcript. Many cell lines, such as the Syrian Hamster AV12 cell line, are incapable of efficiently processing these post-translational modifications therefore the protein C molecules produced in these cell lines are not fully functional. Other cell lines, such as the Human Kidney 293 cell line, produce fully functional protein C molecules but the levels of expression of the protein C molecules in these cell lines are somewhat low. The present invention relates to methods for increasing the level of production of fully functional protein C in those cell lines which do not ordinarily produce fully functional molecules. The invention also relates to methods for increasing the level of total production of protein C molecules in those cell lines which ordinarily produce fully functional molecules. The methods of the present invention concern culturing the protein C producing cell lines at temperatures greater than the common incubation temperature of 37° C.

For purposes of the present invention, as disclosed and claimed herein, the following terms are as defined below.

Adenovirus-transformed cell line—a cell line which expresses the E1A gene product of an adenovirus.

Human protein C—Human protein C zymogen and activated human protein C.

Nascent protein—the polypeptide produced upon translation of an mRNA transcript, prior to any post-translational modifications. However, post-translational modifications such as gamma-carboxylation of glutamic acid residues and hydroxylation of aspartic acid residues may begin to occur before a protein is fully translated from an mRNA transcript.

Protein C Activity—any property of human protein C responsible for proteolytic, amidolytic, esterolytic, and biological (anticoagulant or pro-fibrinolytic) activities. Methods for testing for protein anticoagulant activity are well known in the art, i.e., see Grinnell et.al., 1987, *Bio/Technology* 5:1189–1192.

Zymogen—an enzymatically inactive precursor of a proteolytic enzyme. Protein C zymogen, as used herein, refers to secreted, inactive forms, whether one chain or two chain, of protein C.

All amino acid abbreviations used in this disclosure are those accepted by the United States Patent and Trademark Office as set forth in 37 C.F.R.§1.822(b) (2) (1990).

DETAILED DESCRIPTION OF THE INVENTION

The present invention relates to a method for increasing the production of protein C in an adenovirus-transformed recombinant mammalian host cell. The method comprises culturing the adenovirus-transformed recombinant mammalian host cell at a temperature between about 38° C. and about 39° C. The invention also relates to a method for increasing the production of functional protein C in an adenovirus-transformed recombinant mammalian host cell comprising culturing the host cell at a temperature between about 38° C. and about 39° C.

Many cell lines have been used to produce recombinant human protein C. However, because the human protein C molecule undergoes extensive post-translational modification, most common cell lines either do not produce fully-functional protein C, or, if fully-functional protein C is produced by a cell line, levels of expression or secretion remain relatively low. For example, the Syrian Hamster AV12 cell line generally cannot produce protein C molecules which contain all nine gamma-carboxyglutamic acid residues which are required for full activity. On the other hand, protein C molecules produced in Human Embryonic Kidney 293 cells are generally fully gamma-carboxylated and beta-hydroxylated, yet the levels of production of human protein C from these cell lines is relatively low.

Normally, mammalian cell cultures are incubated at 37° C. When the adenovirus-transformed Syrian Hamster AV12-664 cell line (ATCC CRL 9595) containing a plasmid encoding the human protein C gene was incubated at 37° C., the cell line produced protein C which was only 40% to 50% fully gamma-carboxylated, resulting in low functionality of the protein C in the crude culture medium. When this same cell line was incubated at 38.5° C. to 39° C., the functional anticoagulant activity of the secreted protein C in the conditioned culture medium was increased. The rate of secretion of protein C from this cell line incubated at the elevated temperature was about 20% to 30% lower than the rate of secretion at 37° C., although this decrease in secretion rate is offset by the increase in functionality of the secreted protein C.

Human Kidney 293 cells (ATCC CRL 1573) are transformed primary embryonal human kidney cells which contain and express the transforming gene of Adenovirus 5. These cells have been used to express several important gene products and have been used by a number of different laboratories both in academia and industry. For example, Yan, U.S. Pat. No. 4,981,952 and Bang et. al., U.S. Pat. No. 4,992,373, both disclose the use of the 293 cell line to produce human protein C. The Human Embryonic Kidney 293 cell line secretes fully gamma-carboxylated human protein C when harboring an expression plasmid encoding the human protein C gene. When cultured at 37° C., this 293 cell line secreted recombinant human protein C with a specific activity of approximately 350 U/mg. Increasing the growth temperature of these recombinant 293 cells did not result in an increase in functionality of the secreted protein C (as the protein C from this cell line is already fully gamma-carboxylated). However, the recombinant 293 cells grown at 38° C. to 39° C. demonstrated an increase in the rate of secretion of protein C in comparison to the same cells grown at 37° C. For purposes of the present disclosure, an increase in protein C production can mean either an increase in total protein C secretion from the cell line or an increase in the functionality of the secreted protein C.

The skilled artisan will understand that the present invention is not limited to the use of the adenovirus-transformed Human Embryonic Kidney cell line or the adenovirus-transformed Syrian Hamster AV12-664 cell line. A number of mammalian cell lines are available for the production of human protein C. For example, the HepG2 cell line is a human liver cell line which has been used to produce human protein C. The BHK (Baby Hamster Kidney) cell line, the SA7 cell line, the SV20 cell line, the FAZA cell line and the MK2 cell line have also all been used to produce human protein C. Although not all of the cell lines listed in the preceding sentence are adenovirustransformed cell lines, the skilled artisan understands that many mammalian cell lines can be transformed with the adenovirus to create a specific adenovirus-transformed cell line which can then be used in the method of the present invention.

It should also be understood that the present invention is not limited to only temperatures of 38° C. and 39° C. Most mammalian fermentations are performed at 37° C., yet it has been found that a fermentation temperature of about 38° C. leads to higher production of protein C in adenovirus-transformed cells. In that many fermentation tank and warm-room temperatures may fluctuate up to 0.5° C., the term "about" should be viewed as a temperature within 0.5° C. of the stated temperature. Therefore, the term "about" 38° C. can extend from 37.5C to 38.5° C. Furthermore, the term "about" 39° C. can extend from 38.5° C. to 39.5° C. Most mammalian cells do not grow well once the incubation temperature reaches about 40° C. Preferred temperatures for the method of the present invention range from about 38° C. to about 39° C., while the most preferred embodiment of the present invention is found when the temperature of incubation of the adenovirus-transformed cell line is about 39° C.

The skilled artisan will also recognize that the method of the present invention will allow one to more readily select those clones which are expressing high levels of protein C. For example, as the level of protein C secreted from a cell line is increased, it is easier to assay for the molecule in the crude media, therefore it is easier to select the clone which expresses the highest level of the desired product. The average increase in expression levels for clones isolated at 39° C. ranged from about 69% to 93% in comparison to clones isolated at 37° C.

The following examples are provided as a means of illustrating the present invention and are not to be construed as a limitation thereon.

EXAMPLE 1

Production of Human Protein C in 293 Cells

Recombinant human protein C (rHPC) was produced in Human Kidney 293 cells by techniques well known to the skilled artisan such as those set forth in Yan, U.S. Pat. No. 4,981,952, the entire teaching of which is herein incorporated by reference. The gene encoding human protein C is disclosed and claimed in Bang et al., U.S. Pat. No. 4,775,624, the entire teaching of which is incorporated herein by reference. The plasmid used to express human protein C in 293 cells was plasmid pLPC which is disclosed in Bang et al., U.S. Pat. No. 4,992,373, the entire teaching of which is incorporated herein by reference. The construction of plasmid pLPC is also described in European Patent Publication No. 0 445 939, and in Grinnell et al., 1987, Bio/Technology 5:1189–1192, the teachings of which are also incorporated herein by reference. Briefly, plasmid pLPC was transfected into 293 cells, then stable transformants were identified and subcultured. The clones which demonstrated the highest level of expression were given various designations (e.g., CC35 and CC31-1) and grown under standard cell culture conditions. Alternatively, plasmid pGTC was used to create the stably transformed cell line GT-21. The construction of plasmid pGTC was disclosed in European Patent Publication No. 0 445 939. After growth at 37° C., the human protein C can be separated from the culture fluid by the techniques of Yan, U.S. Pat. No. 4,981,952. The human protein C so produced can be used in the unactivated zymogen form or can be activated by procedures well known to one skilled in the art. The same clones were also grown under the same conditions at 39° C. Results are set forth in Table I.

TABLE I

Effect of growth temperature on the amount of protein C secreted from 293 cells

| Clone | ng/10$^6$/day@37° C. | ng/10$^6$/day@39° C. | Percent increase |
| --- | --- | --- | --- |
| CC35 | 395 | 663 | 68 |
| CC35 | 425 | 664 | 56 |
| GT-21 | 237 | 747 | 215 |
| CC31-1 | 1164 | 2361 | 103 |
| CC35 | 824 | 1227 | 49 |
| CC35 | 2100 | 3906 | 86 |

Even when cells were grown at varying cell densities, thus yielding different expression levels per cell (e.g., CC35), the percent increase in secretion at 39° C. was consistently observed.

EXAMPLE 2

Production of Human Protein C in AV12–664 Cells

Human protein C was produced using plasmid pLPC in substantial accordance with the teachings of Example 1 except Syrian Hamster AV12–664 cells were used rather than Human Embryonic Kidney 293 cells. Functional anticoagulant activity was measured by the techniques of Grinnell et. al, 1987, Bio/Technology 5:1189–1192. Results are set forth in Table II.

TABLE II

Effect of growth temperature on the functional anticoagulant activity of Human Protein C produced in AV12 cells

| Temperature | Units/milligram |
| --- | --- |
| 37° C. | 216 ± 62 |
| 39° C. | 460 ± 19 |

I claim:
1. A method for increasing the production of protein C in an adenovirus-transformed recombinant mammalian host cell said method comprising culturing said adenovirus-transformed recombinant mammalian host cell at a temperature of about 39 ° C., wherein the recombinant mammalian host cell is selected from the group consisting of recombinant AV12 cells and recombinant 293 cells.

2. The method of claim 1 wherein the recombinant mammalian host cell is an AV12 cell.

3. The method of claim 1 wherein the recombinant mammalian host cell is a 293 cell.

4. A method of increasing the level of gammacarboxylation of a recombinantly produced protein C molecule, said method comprising culturing said recombinantly produced protein C molecule in a recombinant AV12 host cell at a temperature of about 39° C.

5. A method of selecting recombinant clones which secrete high levels of protein C, said method comprising culturing adenovirus-transformed recombinant host cells capable of producing protein C at a temperature of about 39° C. then selecting clones which secrete high levels of protein C., wherein the recombinant host cell is selected from the group consisting of recombinant AV12 cells and recombinant 293 cells.

6. The method of claim 5 wherein the recombinant host cell is an AV12 cell.

7. The method of claim 5 wherein the recombinant host cell is a 293 cell.

* * * * *